US 6,512,120 B1
Jan. 28, 2003

(54) METHODS FOR THE SYNTHESIS OF DENSELY FUNCTIONALIZED PYRROLIDINE INTERMEDIATES

(75) Inventors: Pranab Mishra, South Bound Brook, NJ (US); Sengen Sun, San Diego, CA (US); William V. Murray, Belle Mead, NJ (US)

(73) Assignee: Ortho McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/095,674

(22) Filed: Mar. 12, 2002

Related U.S. Application Data

(60) Provisional application No. 60/275,092, filed on Mar. 12, 2001.

(51) Int. Cl.$^7$ .................. C07D 471/04; C07D 491/052; C07D 207/12
(52) U.S. Cl. ................. 546/113; 548/453; 548/531; 548/538; 548/550; 548/551; 548/566; 548/568; 548/572
(58) Field of Search ........................ 546/113; 548/453, 548/531, 538, 550, 551, 566, 568, 572

(56) References Cited

U.S. PATENT DOCUMENTS 5,935,980 A    8/1999   Imperato
6,150,387 A    11/2000  Bohme et al.

FOREIGN PATENT DOCUMENTS

EP      24382        3/1981
WO   WO 0056296     9/2000

OTHER PUBLICATIONS

Wu, Zengru et al; Beijing Daxue Xuebao, Ziran Kexueban 2000, 36 (2), 275–285.
Brummer, Oliver et al; Curr. Opin. Drug Discovery Dev., 2000, 3 (4), 462–473.
Roe, Diana C.; Mol. Diversity Drug Des., 1999, 141–173.
Barnes, Colin et al; Curr. Opin. Chem. Biol., 2000, 4 (3) 346–350.
Weber, Lutz; Curr. Opin. Chem. Biol., 2000, 4 (3), 295–302.
R. A. Owens et al; Biochem. Biophys. Res. Comm., 1991, 181, 402.
P. F. Alewood et al; Tet. Lett., 1992, 33, 977.
E. K. Kick; J.A. Ellman; J. Med. Chem., 1995, 38, 1427.
G. T. Wang et al; J. Med. Chem., 1995, 38, 2995.
J. Jiracek et al; J. Biol. Chem., 1995, 270 21701.
Zuckermann, Ronald N. et al; J. Am. Chem. Soc., 1992 114 (26), 10646–7.
Connolly, P. J. et al; Bioorg. Med. Chem. Lett., 2000, 10 (17), 1995–1999.
Connolly, P. J. et al; Tetrahedron Lett., 2000 41 (27), 5187–5191.
Sun, Sengen et al; J. Org. Chem., 2000, 65 (8), 2555–2559.
Murray, William V. et al; J. Org. Chem., 1999, 64 (16), 5930–5940.
Sun, Sengen; Murray, William V.; J. Org. Chem., 1999, 64 (16), 5941–5945.
Ho, Pak T.; Ngu, Kheh Yong, J. Org. Chem., 1993, 58, 8, 2313–6.
PCT International Search Report, dated Jul. 3, 2002 for PCT Appln. No. PCT/US02/07310 which relates to U.S. application No. 10/095,674, filed Mar. 12, 2002.
A.V.R. Rama et al., Abstract, Beilstein Institut zur Foerderung der Chemischen Wissenschaften 1988–2001, Tetrahedron Let., vol. 32, No. 34, 1991, pp. 43939–4396, XP002202672.
C. Wang et al., "Chemoselective Lactam Formation in the Addition of Benzenesulfonyl Bromide to N–Allyl Acrylamides and N–Allyl 3, 3–Dimethylacrylamides", J. Org. Chem., vol. 64, No. 7, 1999, pp. 2346–2352, XP002202671.
R. Munusamy et al., Abstract, Beilstein Institut zur Foerderung der Chemischen Wissesnschaften 1988–2001, J. Chem. Soc. Perkin. Trans. 2, No. 7, 2001, pp. 1154–1166, XP002202673.

*Primary Examiner*—Bernard Dentz

(57) ABSTRACT

This invention is directed to methods of synthesizing densely functionalized pyrrolidine compounds through the use of intramolecular Diels Alder reactions.

34 Claims, No Drawings

METHODS FOR THE SYNTHESIS OF DENSELY FUNCTIONALIZED PYRROLIDINE INTERMEDIATES

CROSS REFERENCE TO RELATED APPLICATIONS

This application claims benefit of provisional application Serial Number 60/275,092, filed Mar. 12, 2001, which is hereby incorporated by reference.

FIELD OF THE INVENTION

This invention is directed to a method for synthesizing densely functionalized pyrrolidine intermediates. In particular, the invention is directed to a method for synthesizing highly substituted pyrrolidine intermediates both on and off solid supports. More particularly, the invention is directed to highly substituted pyrrolidine intermediates useful for the further in situ and resin-bound synthetic generation of chemical libraries.

BACKGROUND OF THE INVENTION

Compounds having biological activity can be identified by screening diverse collections of compounds (i.e., libraries of compounds) produced through molecular biology techniques or synthetic chemical techniques.

Pharmaceutical drug discovery relies heavily on studies of structure-activity relationships wherein the structure of "lead compounds" is typically altered to determine the effect of the alteration on activity. Alteration of the structure of the lead compound around a core "scaffold" structure creates a plurality of compounds and permits evaluation of the effect of the structural alteration on activity.

The "library" of compounds thus created is derived from a single lead compound. Accordingly, a plurality of scaffolds and libraries can be created and screened by modifying the core of the lead compound and repeating the screening procedures. In this manner, compounds with the best biological profile, i.e. those that are most active and which have the most ideal pharmacologic and pharmacokinetic properties, can be quickly identified from the initial lead compound.

The generation of chemical libraries both on and off solid resins have proven to be a valuable resource for the pharmaceutical industry in their endeavors to discover new drugs using high throughput screening techniques (Wu, Zengru et al, *Beijing Daxue Xuebao, Ziran Kexueban* 2000, 36(2), 275–285; Brummer, Oliver et al, *Curr. Opin. Drug Discovery Dev.*, 2000, 3(4), 462–473; Roe, Diana C., *Mol. Diversity Drug Des.*, 1999, 141–173; Barnes, Colin et al, *Curr. Opin. Chem. Biol.*, 2000, 4(3), 346–350; Weber, Lutz, *Curr. Opin. Chem. Biol.*, 2000, 4(3), 295–302).

In creating the libraries, the compounds are ideally synthesized on a solid support (resin-bound) or in solution phase (in situ or off-solid support). Relatively simple synthetic methods to produce a diverse collection of such derivatives in situ, though, are often not available.

The need for large numbers of compounds has led to the synthesis of compounds based on very simple templates. A number of peptidomimetic libraries based on amino acid modules have also been introduced (R. A. Owens et al, *Biochem. Biophys. Res. Comm.*, 1991, 181, 402; P. F. Alewood et al, *Tet. Lett.*, 1992, 33, 977; E. K. Kick and J. A. Ellman, *J. Med. Chem.*, 1995, 38, 1427; G. T. Wang et al, *J. Med. Chem.*, 1995, 38, 2995; J. Jiracek et al, *J. Biol. Chem.*, 1995, 270 21701). Chiron's peptoid approach led to a number of interesting starting points for analogs early in the library generation era (Zuckermann, Ronald N. et al, *J. Am. Chem. Soc.*, 1992, 114(26), 10646–7). Amino acid based libraries have been used to address protein-protein interactions as well (Connolly, P. J. et al, *Bioorg. Med. Chem. Lett.*, 2000, 10(17), 1995–1999; Connolly, P. J. et al, *Tetrahedron Lett.*, 2000, 41(27), 5187–5191). Unfortunately, some of the more simple libraries have not yielded compounds that demonstrate significant biological activity.

More recently efforts have been made to develop chemistry that is amenable to library generation that produces molecules of considerable complexity for the purpose of creating more diverse chemical libraries. Recently electrocyclic reactions of amino acid derived dienes have been used to produce densely funtionalized octahydroquinolines and hexahydroisoindoles (Sun, Sengen et al, *J. Org. Chem.*, 2000, 65(8), 2555–2559; Murray, William V. et al, *J. Org. Chem.*, 1999, 64(16), 5930–5940; Sun, Sengen and Murray, William V., *J. Org. Chem.*, 1999, 64(16), 5941–5945). Diels Alder reactions are useful synthetic methods either on or off solid support and allow for control of facial selectivity, endo versus exo selectivity and stereochemical selectivity at most of the ring positions.

Pyrrolidines are a class of molecules that have demonstrated diverse biological activity. PCT publication WO0056296 (published Sep. 28, 2000) describes substituted pyrrolidine compounds as dipeptidyl peptidase IV inhibitors for use in improving fertility. U.S. Pat. No. 5,935,980 (PCT publication WO9638139, published Dec. 5, 1996) describes substituted pyrrolidine compounds for use in treating alcoholism and associated conditions. U.S. Pat. No. 6,150,387 (PCT publication WO9728798, published Aug. 14, 1997) describes substituted pyrrolidine compounds for use in preventing or reducing drug dependence, pharmacomania or substance abuse and as useful CCK (cholecystokinin) and gastric receptor inhibitors for treating or preventing psychoses, anxiety disorders, Parkinson's disease, tardive dyskinesia, irritable bowel syndrome, acute pancreatitis, ulcers, disorders of intestinal motility and certain CCK-sensitive tumors and as useful appetite regulators and analgesics. European patent application EP 24382 (published Mar. 4, 1981) describes substituted piperidine derivatives for use as local and topical anesthetics or for use as antiarrythmic agents.

Accordingly, in order to develop new pharmaceutical drugs to treat various disease conditions, it would be highly desirable to be able to generate libraries of diverse pyrrolidine derivatives optionally attached to a solid support. An object of the present invention is to provide a facile in situ and resin-bound method for the generation of a multiplicity of densely functionalized pyrrolidine intermediates.

SUMMARY OF THE INVENTION

The present invention is directed to a method for generating densely functionalized pyrrolidine intermediates through the use of intramolecular Diels Alder reactions (via cycloaddition directed remote hydroxylation or amination) both on and off a solid support.

Accordingly, the present invention is directed to a method for generating densely functionalized pyrrolidine intermediates selected from the group consisting of Formula (I) and Formula (II):

Formula (I)

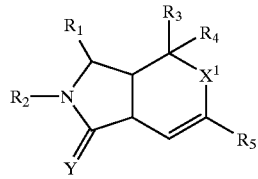

Formula (II)

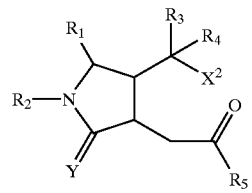

wherein $R_1$ is selected from the group consisting of a standard, natural (L) and non-natural (D), non-hydrogen amino acid side chain (wherein the amino acid side chain is optionally substituted with a suitable protecting group), hydrogen and —($C_{1-8}$)alkyl {wherein $C_{1-8}$alkyl is optionally substituted with 1 to 2 substituents selected from the group consisting of —$CO_2H$ (wherein $CO_2H$ is optionally substituted with a suitable protecting group), -phenyl-$R_6$, -heteroaryl-$R_6$ and hydroxy (wherein hydroxy is optionally substituted with a suitable protecting group)}; alternatively, $R_1$ and $R_2$ may be joined to form a heterocyclyl ring;

$R_6$ is one to two substituents selected from the group consisting of hydrogen, —($C_{1-8}$)alkyl, —O—($C_{1-8}$)alkyl, halogen, hydroxy and nitro;

$R_2$ is selected from the group consisting of hydrogen (wherein hydrogen is optionally replaced with a suitable protecting group), —($C_{1-8}$)alkyl, —($C_{1-8}$)alkyl-Ph—$R_6$, —C(O)—($C_{1-8}$)alkyl, —C(O)—Ph—$R_6$, —C(O)O—($C_{1-8}$)alkyl, —C(O)O—Ph—$R_6$, —C(O)O—($C_{1-8}$)alkyl-Ph—$R_6$ and —$SO_2$—Ph—$R_6$;

$R_3$ is selected from the group consisting of —C(O)—N($R_7R_8$), —$CO_2H$ (wherein $CO_2H$ is optionally substituted with a suitable protecting group), —C(O)—O—($C_{1-8}$)alkyl and cyano;

$R_7$ is selected from hydrogen, —($C_{1-8}$)alkyl, —($C_{1-8}$)alkyl-Ph—$R_6$, hydroxy (wherein hydroxy is optionally substituted with a suitable protecting group) or a suitable protecting group;

$R_8$ is selected from hydrogen, —($C_{1-8}$)alkyl, —($C_{1-8}$)alkyl-Ph—$R_6$ or a suitable protecting group;

$R_4$ is selected from the group consisting of hydrogen, —($C_{1-8}$)alkyl and —($C_{1-8}$)alkyl-Ph—$R_6$;

$R_5$ is selected from the group consisting of —($C_{1-8}$)alkyl and —Ph—$R_6$;

Y is optionally present and is selected from the group consisting of O and S;

$X^1$ is selected from the group consisting of —O—, —N(H)— (wherein NH is optionally substituted with a suitable protecting group), —N(—OH)— (wherein hydroxy is optionally substituted with a suitable protecting group), —N(—O—($C_{1-8}$)alkyl)—, —N(—$C_{1-8}$alkyl-aryl-$R_6$)— and —N(—O—($C_{1-8}$)alkyl-aryl-$R_6$)—; and, $X^2$ is selected from the group consisting of —OH (wherein OH is optionally substituted with a suitable protecting group), —$NH_2$ (wherein $NH_2$ is optionally substituted with a suitable protecting group), —NH(—OH) (wherein NH and OH are optionally substituted with a suitable protecting group), —NH(—$C_{1-8}$alkyl) (wherein NH is optionally substituted with a suitable protecting group) and —NH(—$C_{1-8}$alkyl-aryl-$R_6$) (wherein NH is optionally substituted with a suitable protecting group);

and pharmaceutically acceptable salts and diastereomers thereof;

wherein the method for generating an intermediate selected from the group consisting of Formula (I) and Formula (II) is either a resin-bound or an in-situ method comprising:

(a) preparing a compound of Formula (III):

Formula (III)

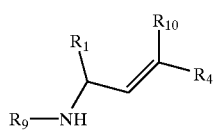

(prepared as described in Sun, Sengen et al, *J. Org. Chem.*, 2000, 65(8), 2555–2559; Murray, William V. et al, *J. Org. Chem.*, 1999, 64(16), 5930–5940; Sun, Sengen and Murray, William V., *J. Org. Chem.*, 1999, 64(16), 5941–5945) wherein $R_1$ and $R_4$ are as previously described; wherein $R_9$ is selected from $R_2$ (for an in-situ method) or (for a resin-bound method) is selected from —$SO_2$—Ph—$CO_2$— (resin) or —$SO_2$—Ph—C (O)—NH— (resin); and, wherein $R_{10}$ is selected from $R_3$ (for an in-situ method) or (for a resin-bound method) is selected from —$CO_2$— (resin), —C(O)—NH— (resin) or —C(N)-(resin); and, (b) acylating the compound of Formula (III) to prepare a compound of Formula (IV):

Formula (IV)

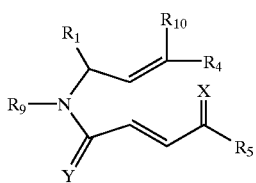

wherein Y, $R_1$, $R_4$, $R_5$, $R_9$ and $R_{10}$ are as previously described; and, wherein X is selected from the group consisting of O, N(H) (wherein NH is optionally substituted with a suitable protecting group), N(—OH) (wherein hydroxy is optionally substituted with a suitable protecting group), N(—O—($C_{1-8}$)alkyl), N(—$C_{1-8}$alkyl-aryl-$R_6$) and N(—O—($C_{1-8}$)alkyl-aryl-$R_6$);

(c) reacting the compound of Formula (IV) (with the proviso that the method is a resin-bound method) with the appropriate starting materials, using the appropriate reagents and conditions and cleaving the compound of Formula (IV) (with the proviso that the method is a resin-bound method) from the resin to prepare the intermediate selected from the group consisting of Formula (I) and Formula (II); or, (d) refluxing the compound of Formula (IV) (with the proviso that the method is an in-situ method) using the appropriate reagents and conditions to prepare the intermediate selected from the group consisting of Formula (I) and Formula (II); wherein the intermediate is selected from a kinetic product (a trans isomer prepared at a reflux temperature of ≦80° C.) or a thermodynamic product (a cis isomer prepared at a reflux temperature of >80° C.);

alternatively, the method for preparing an intermediate of Formula (I) further comprises preparing a compound selected from Formula (IV) wherein X is NH(—OH); and, adding silica gel in the appropriate amount at the appropriate time and temperature to prepare the intermediate of Formula (I) by cycloaddition; and, alternatively, the method for preparing an intermediate of Formula (II) further comprises hydrolyzing an intermediate of Formula (I) under the appropriate conditions to prepare the intermediate of Formula (II).

This invention is also directed to the use of the instant methods to prepare densely funtionalized pyrrolidine intermediates for use in synthesizing compound libraries.

DETAILED DESCRIPTION OF THE INVENTION

Embodiments of the present invention include intermediates selected from the group consisting of Formula (I) and Formula (II) wherein, preferably, $R_1$ is selected from the group consisting of a standard, natural (L) and non-natural (D), non-hydrogen amino acid side chain (wherein the amino acid side chain is optionally substituted with a suitable protecting group), hydrogen and —$(C_{1-4})$alkyl {wherein $C_{1-4}$alkyl is optionally substituted with 1 to 2 substituents selected from the group consisting of —$CO_2H$ (wherein $CO_2H$ is optionally substituted with a suitable protecting group), -phenyl-$R_6$, -heteroaryl-$R_6$ and hydroxy (wherein hydroxy is optionally substituted with a suitable protecting group)}; alternatively, $R_1$ and $R_2$ may be joined to form a heterocyclyl ring.

More preferably, $R_1$ is selected from a standard, natural (L) and non-natural (D), non-hydrogen amino acid side chain optionally substituted with a suitable protecting group.

Preferably, when $R_1$ is selected from a standard, natural (L) and non-natural (D), non-hydrogen amino acid side chain optionally substituted with a suitable protecting group, the amino acid side chain is selected from Ala, Val, Phe, Tyr, Ser, Thr, Asp, Glu and His.

Embodiments of the present invention include intermediates selected from the group consisting of Formula (I) and Formula (II) wherein, preferably, $R_6$ is one to two substituents selected from the group consisting of hydrogen, —$(C_{1-4})$alkyl, —O—$(C_{1-4})$alkyl, halogen, hydroxy and nitro.

More preferably, $R_6$ is one to two substituents selected from the group consisting of hydrogen, —O—$(C_{1-4})$alkyl, halogen and nitro.

Most preferably, $R_6$ is one to two substituents selected from the group consisting of hydrogen, methoxy, bromine and nitro.

Embodiments of the present invention include intermediates selected from the group consisting of Formula (I) and Formula (II) wherein, preferably, $R_2$ is selected from the group consisting of hydrogen (wherein hydrogen is optionally replaced with a suitable protecting group), —$(C_{1-4})$alkyl, —$(C_{1-4})$alkyl-Ph—$R_6$, —C(O)—$(C_{1-4})$alkyl, —C(O)—Ph—$R_6$, —C(O)O—$(C_{1-4})$alkyl, —C(O)O—Ph—$R_6$, —C(O)O—$(C_{1-4})$alkyl-Ph—$R_6$ and —$SO_2$—Ph—$R_6$.

More preferably, $R_2$ is selected from the group consisting of —$(C_{1-4})$alkyl, —$(C_{1-4})$alkyl-Ph—$R_6$, —C(O)O—$(C_{1-4})$alkyl, —C(O)O—$(C_{1-4})$alkyl-Ph—$R_6$ and —$SO_2$—Ph—$R_6$.

Most preferably, $R_2$ is selected from —$(C_{1-4})$alkyl-Ph—$R_6$.

Embodiments of the present invention include intermediates selected from the group consisting of Formula (I) and Formula (II) wherein, preferably, $R_3$ is selected from the group consisting of —C(O)—$N(R_7R_8)$, —$CO_2H$ (wherein $CO_2H$ is optionally substituted with a suitable protecting group), —C(O)—O—$(C_{1-4})$alkyl and cyano.

More preferably, $R_3$ is selected from the group consisting of —$CO_2H$ (wherein $CO_2H$ is optionally substituted with a suitable protecting group), —C(O)—O—$(C_{1-4})$alkyl and cyano.

Most preferably, $R_3$ is selected from —C(O)—C—$(C_{1-4})$alkyl.

Embodiments of the present invention include intermediates selected from the group consisting of Formula (I) and Formula (II) wherein, preferably, $R_7$ is selected from hydrogen, —$(C_{1-4})$alkyl, —$(C_{1-4})$alkyl-Ph—$R_6$, hydroxy (wherein hydroxy is optionally substituted with a suitable protecting group) or a suitable protecting group.

More preferably, $R_7$ is selected from hydrogen, —$(C_{1-4})$alkyl or a suitable protecting group.

Most preferably, $R_7$ is hydrogen.

Embodiments of the present invention include intermediates selected from the group consisting of Formula (I) and Formula (II) wherein, preferably, $R_8$ is selected from hydrogen, —$(C_{1-4})$alkyl, —$(C_{1-4})$alkyl-Ph—$R_6$ or a suitable protecting group.

More preferably, $R_8$ is selected from hydrogen, —$(C_{1-4})$alkyl or a suitable protecting group.

Most preferably, $R_8$ is hydrogen.

Embodiments of the present invention include intermediates selected from the group consisting of Formula (I) and Formula (II) wherein, preferably, $R_4$ is selected from the group consisting of hydrogen, —$(C_{1-4})$alkyl and —$(C_{1-4})$alkyl-Ph—$R_6$.

More preferably, $R_4$ is selected from the group consisting of hydrogen and —$(C_{1-4})$alkyl.

Most preferably, $R_4$ is hydrogen.

Embodiments of the present invention include intermediates selected from the group consisting of Formula (I) and Formula (II) wherein, preferably, $R_5$ is selected from the group consisting of —$(C_{1-4})$alkyl and —Ph—$R_6$.

Embodiments of the present invention include intermediates selected from the group consisting of Formula (I) and Formula (II) wherein, preferably, Y is present and is selected from the group consisting of O and S.

More preferably, Y is present and is O.

Embodiments of the present invention include intermediates selected from the group consisting of Formula (I) and Formula (II) wherein, preferably, $X^1$ is selected from the group consisting of —O—, —N(H)—, (wherein NH is optionally substituted with a suitable protecting group), —N(—OH)— (wherein hydroxy is optionally substituted with a suitable protecting group), —N(—O—(C$_{1-4}$)alkyl)—, —N(—C$_{1-4}$alkyl-aryl-R$_6$)— and —N(—O—(C$_{1-4}$)alkyl-aryl-R$_6$)—.

More preferably, X$^1$ is selected from the group consisting of —O— and —N(—OH)— (wherein hydroxy is optionally substituted with a suitable protecting group).

Most preferably, X$^1$ is selected from the group consisting of —O— and —N(—OH)—.

Embodiments of the present invention include intermediates selected from the group consisting of Formula (I) and Formula (II) wherein, preferably, X$^2$ is selected from the group consisting of OH (wherein OH is optionally substituted with a suitable protecting group), —NH$_2$ (wherein NH$_2$ is optionally substituted with a suitable protecting group), —NH(—OH) (wherein NH and OH are optionally substituted with a suitable protecting group), —NH(—C$_{1-4}$alkyl) (wherein NH is optionally substituted with a suitable protecting group) and —NH(—C$_{1-4}$alkyl-aryl-R$_6$) (wherein NH is optionally substituted with a suitable protecting group).

More preferably, X$^2$ is selected from the group consisting of OH (wherein OH is optionally substituted with a suitable protecting group), —NH(—OH) (wherein NH and OH are optionally substituted with a suitable protecting group) and —NH(—C$_{1-4}$alkyl-aryl-R$_6$) (wherein NH is optionally substituted with a suitable protecting group).

Embodiments of the present invention include intermediates selected from Formula (I) wherein the intermediate is selected from Formula (Ia):

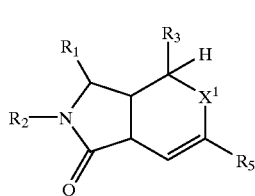

Formula (Ia)

wherein X$^1$, R$_1$, R$_2$, R$_3$ and R$_5$ are dependently selected from the up consisting of:

| Cpd | X$^1$ | R$_1$ | R$_2$ | R$_3$ | R$_5$ |
|---|---|---|---|---|---|
| 1 | —O— | —CH$_2$Ph | —CH$_2$Ph | —C(O)OEt | CH$_3$; |
| 2 | —O— | —CH$_2$Ph | —CH$_2$Ph | —C(O)OEt | Ph; |
| 3 | —N(OH)— | —CH$_2$Ph | —CH$_2$Ph | —C(O)OEt | CH$_3$; |
| 4 | —N(OH)— | —CH$_2$Ph | —CH$_2$Ph | —C(O)OEt | Ph; |
| 5 | —N(OH)— | —CH$_2$Ph | —CH$_2$Ph | —C(O)OH | CH$_3$; |

-continued

| Cpd | X$^1$ | R$_1$ | R$_2$ | R$_3$ | R$_5$ |
|---|---|---|---|---|---|
| 6 | —O— | —CH(CH$_3$)$_2$ | —CH$_2$Ph | —C(O)OEt | CH$_3$; |
| 7 | —O— | —CH(CH$_3$)$_2$ | —CH$_2$Ph | —C(O)OEt | Ph; |
| 8 | —O— | —CH$_2$Ph | —CH$_2$(4-Br)Ph | —C(O)OEt | Ph; |
| 9 | —O— | —CH$_2$Ph | —CH$_2$(4-Br)Ph | —C(O)OEt | CH$_3$; | and pharmaceutically acceptable salts and diastereomers thereof.

Embodiments of the present invention include intermediates selected from Formula (II) wherein an intermediate is selected from Formula (IIa):

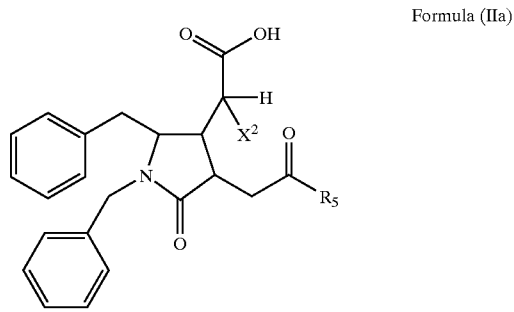

Formula (IIa)

wherein X$^2$ and R$_5$ dependently selected from the group consisting of:

| Cpd | X$^2$ | R$_5$ |
|---|---|---|
| 10 | —OH | CH$_3$; |
| 11 | —NH—CH$_3$ | CH$_3$; |
| 12 | —OH | Ph; |
| and, | | |
| 13 | —NH—CH$_3$ | Ph; | and pharmaceutically acceptable salts and diastereomers thereof.

Embodiments of the present invention include compounds selected from Formula (IV) wherein a compound is selected from Formula (IVa):

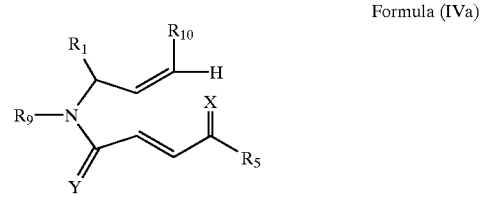

Formula (IVa)

wherein X, R$_1$, R$_5$, R$_9$ and R$_{10}$ are dependently selected from the group consisting of:

| Cpd | X | R$_1$ | R$_5$ | R$_9$ | R$_{10}$ |
|---|---|---|---|---|---|
| I1 | O | —CH$_2$Ph | —CH$_3$ | —CH$_2$Ph | —CO$_2$—CH$_2$—CH$_3$; |
| I2 | N(OH) | —CH$_2$Ph | —CH$_3$ | —CH$_2$Ph | —CO$_2$—CH$_2$—CH$_3$; |
| I3 | O | —CH$_2$Ph | —Ph | —CH$_2$Ph | —CO$_2$—CH$_2$—CH$_3$; |

-continued

| Cpd | X | $R_1$ | $R_5$ | $R_9$ | $R_{10}$ |
|---|---|---|---|---|---|
| I4 | O | —CH(CH$_3$)$_2$ | —CH$_3$ | —CH$_2$Ph | —CO$_2$—CH$_2$—CH$_3$; |
| I5 | O | —CH(CH$_3$)$_2$ | —Ph | —CH$_2$Ph | —CO$_2$—CH$_2$—CH$_3$; |
| I6 | O | —CH(CH$_3$)$_2$ | —CH$_3$ | —CH$_2$(4-Br)Ph | —CO$_2$—CH$_2$—CH$_3$; |
| I7 and, | O | —CH(CH$_3$)$_2$ | —Ph | —CH$_2$(4-Br)Ph | —CO$_2$—CH$_2$—CH$_3$; |
| I8 | | —CH$_2$Ph | —CH$_3$ | —CH$_2$Ph | —CO$_2$—CH$_2$—CH$_3$; | and pharmaceutically acceptable salts and enantiomers thereof.

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201–217; *J. Pharm.Sci.*, 1997 (Jan), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The compounds according to this invention possess one or more chiral centers and thus may exist as enantiomers, diastereomers and enantiomer/diastereomers. Where the processes for the preparation of the present compounds give rise to a mixture of such isomers, the isomers may be separated by conventional techniques such as preparative chromatography. Alternatively, the isomers may be resolved using a chiral HPLC column. It is to be understood that all such isomers and mixtures thereof are encompassed within the scope of the present invention.

Unless specified otherwise, the term "alkyl" refers to a saturated straight or branched chain consisting solely of 1–8 hydrogen substituted carbon atoms; and, preferably, 1–4 hydrogen substituted carbon atoms. The term "alkoxy" refers to —O—alkyl, where alkyl is as defined supra. Unless indicated otherwise, alkyl chains are optionally substituted within the alkyl chain or on a terminal carbon atom with 1 to 2 substituents.

The term "heterocyclyl" refers to a saturated ring having five or six members of which at least one member is a N atom and which optionally contains one additional N atom. Examples include, and are not limited to, pyrrolidinyl, imidazolidinyl or pyrazolidinyl.

The term "aryl" refers to an aromatic monocyclic ring containing 6 hydrogen substituted carbon atoms such as phenyl.

The term "suitable protecting group" as used herein refers to any of the known terminal moieties for protecting amino or hydroxy subsituents used in the art of organic synthesis as, for example, described in *Principles of Peptide Synthesis*, 2$^{nd}$ Ed., M. Bodanszky, Springer-Verlag, Berlin (1993); *The Peptides*, Vol 3, *Protection of Functional Groups in Peptide Synthesis*, eds E. Gross and J. Meienhofer, Academic Press, New York (1981); and, *Protective Groups in Organic Synthesis*, 2$^{nd}$ Ed., T. W. Greene and P. G. M. Wuts, John Wiley & Sons, New York, (1991); which are hereby incorporated by reference.

When an amino acid side chain is optionally substituted with a suitable protecting group, the amino acid side chain will have amino or hydroxy substituents thus protected.

Examples of suitable protecting groups for substitution on a hydroxy substituent include, and are not limited to, methyl, benzyl, 2,4-(MeO$_2$)benzyl, tetrahydropyranyl, tri(C$_{1-6}$) alkylsilyl (such as trimethylsilyl (TMS) or triethylsilyl (TES)), t-butyl, 2-methoxyethoxymethyl (MEM), 4-(dimethylcarbamoyl)benzyl and phenoxyacetyl ethers. The hydroxy protecting group selected is preferably one that is easily removed in the reaction process.

Examples of suitable protecting groups for substitution on an amino substituent include, and are not limited to, acetyl (Ac), benzoyl (Bz), trifluoroacetyl (Tfa), toluenesulfonyl (Tos), benzyl (Bn), 2,4-(MeO$_2$)benzyl, dibenzyl, triphenylmethyl (Trt), 2-(nitro)Ph-sulfenyl (Nps), benzyloxycarbonyl (Cbz or Z), t-butoxycarbonyl (Boc), allyloxycarbonyl (Alloc), 9-fluorenylmethoxycarbonyl (Fmoc), 2-(bromo)benzyloxycarbonyl (2-Br-Z), 2-(chloro)benzyloxycarbonyl (2-Cl-Z), t-butyl-dimethylsilyloxycarbonyl, [2-(3,5-dimethoxyphenyl)-propyl-2-oxycarbonyl] (Ddz), 2,2,2-(trichloro)ethyloxycarbonyl (Troc), biphenylisopropyloxycarbonyl (Bpoc) and 2-(nitro)benzyloxycarbonyl.

The term "independently" means that when more than one substituent is selected from a group, the substituents selected may be the same or different. "Dependently" means that the substituents are specified in an indicated combination of structure variables.

The methods described above can be used to a plurality of intermediates from which a library of diverse pyrrolidine derivatives can be created.

This specification refers to substituents selected from a standard, natural (L) and non-natural (D), non-hydrogen amino acid side chain. The term "natural (L)" refers to those amino acids having a "Levo" enantiomeric configuration and the term "non-natural (D)" refers to those amino acids having a "Dextro" enantiomeric configuration. In addition, certain abbreviations are used to refer to the amino acid side chains having the following meanings:

| | |
|---|---|
| Ala | Alanine |
| Arg | Arginine |
| Asn | Asparagine |
| Asp | Aspartic acid |
| Cys | Cysteine |
| Gln | Glutamine |
| Glu | Glutamic acid |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |

Throughout this specification, certain other abbreviations are employed having the following meanings, unless specifically indicated otherwise:

| | |
|---|---|
| "Cpd" | Compound |
| "Ph" | Phenyl |
| "Me" | Methyl |
| "Bn" | Benzyl |
| "Boc" | t-Butoxycarbonyl |
| "Fmoc" | 9-fluorenylmethoxycarbonyl) |
| "Tosyl" | 2,2,2-(trichloro)-1,1-Ethanediol |
| "Nosyl" | 4-(Nitro)benzenesulfonyl |
| "Mesyl" | Methanesulfonyl |
| "DMF" | N,N-Dimethylformamide |
| "THF" | Tetrahydrofuran |
| "TFA" | Trifluoroacetic acid |
| "EDCI" | 1-(3-Dimethylaminopropyl)-3-ethylcarbodiimide |
| "HOAT" | 3-hydroxy-3H-1,2,3-Triazolo[4,5-b]pyridine |
| "TMOF" | Trimethyl-o-formate |
| "DIEA" | N,N-diisopropylethylamine |
| "HATU" | o-(7-Azabenzotriazol-1-yl)-1,1,3,3-tetramethyluronium |
| "KOtBu" or "t-BuOK" | Potassium Tertiary Butoxide |
| "MeOH" | Methanol |

General Synthetic Methods

The generation of chemical libraries on and off resin has proven to be a valuable resource for the pharmaceutical industry in their endeavors to discover new drugs from High Throughput screening. The current invention provides an invention process that allows for the assembly of highly complex drug-like molecules with defined stereochemistry. The key step of this invention is an Intramolecular Diels Alder reaction that allows most positions of the pyrrolidine to be easily modified.

In accordance with the invention, novel amino-acid derived triene precursors are prepared, on or off a solid support. These triene precursors undergo a Diels Alder cycloaddition reaction in situ, to yield the complex pyrrolidine intermediates which may be used to further prepare compound libraries.

Resin-bound or off-resin N-protected amino acid ester compounds used in the present methods are prepared according to methods known in the art (Sun, et al, *J. Org. Chem.*, 1999, 64, 16, 5930–5940 and 5941–5945; Sun, et al, *J. Org. Chem.*, 2000, 65, 2555–2559; Murray, et al, *J. Org. Chem.*, 1999, 64 5930–5940) which are incorporated herein by reference.

Scheme A

Off-Resin Synthesis

An N-protected amino acid ester Compound A1 was acylated with a substituted acrylic acid Compound A2 using the appropriate solvents and conditions for a time period of from about 1 to about 10 hours at an appropriate temperature. The product was the amino-protected triene intermediate of Formula (Ic).

The triene Compound A3 was raised to an appropriate reflux temperature in an appropriate reflux solvent for a time period of from about 10 to about 168 hours to yield either the cyclized intermediate of Formula (I) or the ring opened pyrrolidine intermediate of Formula (II).

The cyclized intermediate of Formula (I) may also be prepared by a cycloaddition reaction forced by the addition of silica gel to the reaction mixture containing Compound A3. The ring opened intermediate of Formula (II) may also be prepared by further hydrolyzing the intermediate of Formula (I).

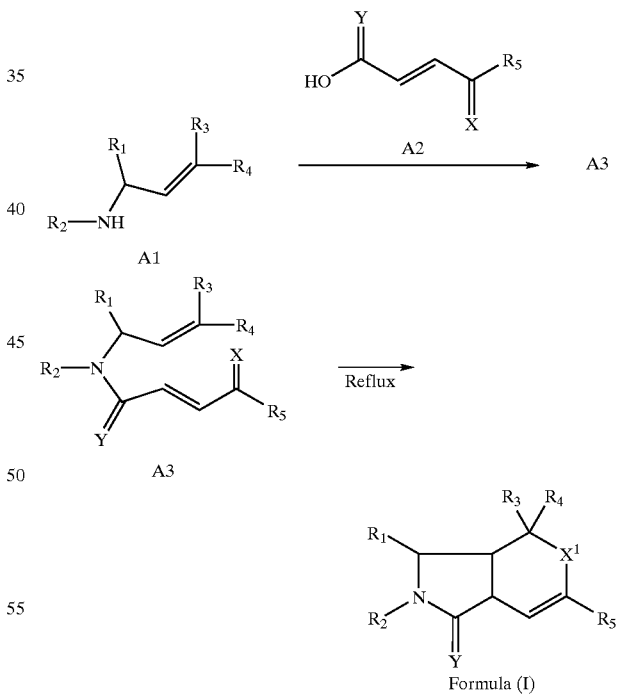

Scheme B

Off-Resin Synthesis

For a compound selected from Formula (I), such as Compound B1 or Compound B2, the reflux temperature, solvent and time period is used to selectively determine the diastereomeric configuration of the 3a and 7a hydrogen atoms.

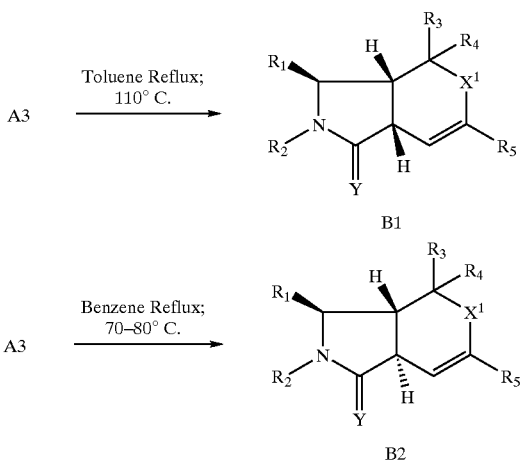

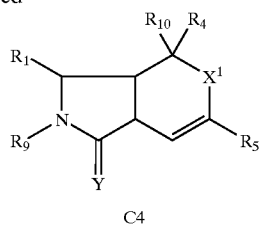

To prepare an isomeric intermediate of the present invention, the stereospecific nature of the starting materials used to prepare Compound C1 and reacted with Compound C3 selectively determine the diastereomeric configuration of the resulting intermediate selected from the group consisting of Formula (I) and Formula (II).

Similarly, for a compound selected from Formula (II), the choice of reflux temperature, solvent and time period is used to selectively determine the diastereomeric configuration of the hydrogen atoms on the 3 and 4 position of the pyrrolidinyl ring and the diastereomeric configuration of $X^2$, $R_3$ and $R_4$.

Specific Synthetic Methods

Nomenclature

Compounds are named according to nomenclature well known in the art and such nomenclature is exemplified using ring numbering as follows:

Scheme C

Resin-Bound Synthesis

To prepare Compound C3, a resin-bound N-protected amino acid ester Compound C1 (where $R^9$ is not selected from $R^2$ and $R^{10}$ is not selected from $R^3$) was acylated with a substituted acrylic acid Compound C2 using the appropriate solvents and conditions and shaken for an appropriate time at room temperature.

The triene Compound C3 was closed by a Diels Alder cycloaddition reaction to form the cyclized Compound C4, which was then removed from the resin as the intermediate of Formula (I). The ring opened pyrrolidine intermediate of Formula (II) is further prepared by hydrolysis of the cyclized intermediate of Formula (I).

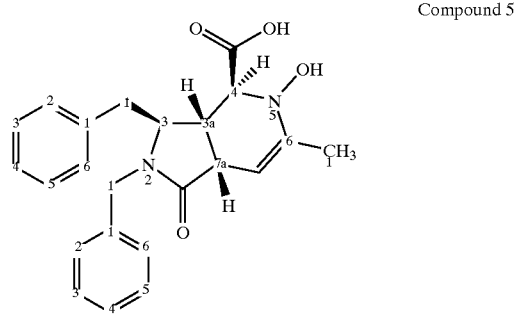

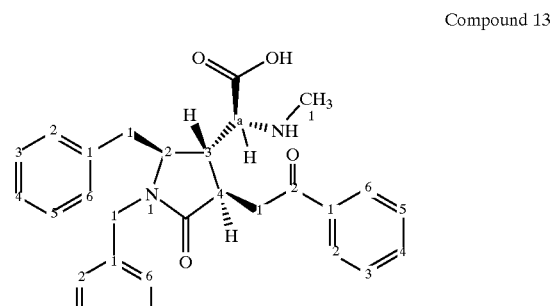

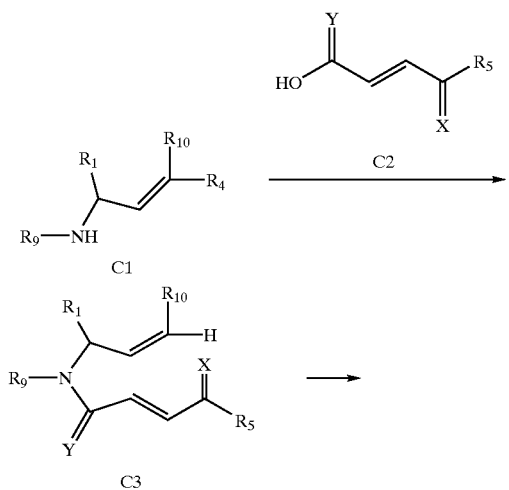

| (3S,3aR,4S,7aR)-2,3,3a,4,5,7a-Hexahydro-5-hydroxy-6-methyl-1-oxo-2,3-bis(phenylmethyl)-1H-pyrrolo[3,4-c]pyridine-4-carboxylic acid | ($\alpha^3$R,2S,3S,4R)-$\alpha$-(Methylamino)-5-oxo-4-(2-oxo-2-phenylethyl)-1,2-bis(phenylmethyl)-3-pyrrolidineacetic acid |
|---|---|

Compound names can be generated using a nomenclature system based on these examples or may be generated using commercial chemical naming software such as the ACD/Index Name (Advanced Chemistry Development, Inc., Toronto, Ontario).

The following examples are set forth to illustrate the claimed invention and are not to be construed as a limitation thereof.

EXAMPLE 1

(3S,3aR,4S,7aR)-1,2,3,3a,4,7a-hexahydro-6-methyl-1-oxo-2,3-bis(phenylmethyl)-pyrano[3,4-c]pyrrole-4-carboxylic acid ethyl ester (Cpd 1)

Off Resin Synthesis t-BuOK (1M in THF, 41 mL) was slowly added to a 0–5° C. solution of triethyl phosphono acetate (8 mL, 40.3 mmol) in THF (100 mL). The reaction mixture was stirred at 0° C. for 1 hr and an N-Boc protected aldehyde (10.03 g, 40.3 mmol, dissolved in 50 mL THF) (prepared as described in Sun, et al, *J. Org. Chem.*, 1999, 64, 16, 5930–5940 and 5941–5945; and, Sun, et al, *J. Org. Chem.*, 2000, 65, 2555–2559) was slowly added to the reaction vessel at 0° C. The mixture was then stirred for 2 hours at 0° C. and was slowly warmed up to room temperature. The reaction mixture was then stirred at room temperature for 6 hrs, cooled down to 0° C. and quenched with ice-cold 1N HCl. After extraction with EtOAc (3×75 mL) and flash chromatography using 10–20% EtOAc/Hexane, Compound 1A was isolated (11.2 g, 35.1 mmol, 87%). $^1$H NMR δ: 1.22 (t, J=7.2, 3H), 1.33 (s, 9H), 2.72 (m, 2H), 4.15 (q, J=7.2, 4H), 4.42 (m, 1H), 5.72 (m, J=17.6), 6.81 (m, J=14.7, J=5.8). $^{13}$C NMR δ: 28.2, 40.8, 52.3, 60.2, 79.8, 121.1, 126.8, 128.5, 129.4, 129.5, 130.4, 136.4, 147.6, 150, 154.9, 166.1. LC/MS expected mass: 319.2, Na salt 342,2, observed mass 342.2.

25 mL of TFA in $CH_2Cl_2$ (1:1) at 0° C. was added to a solution of the Boc-protected ester Compound 1A, (3.5 g, 10.9 mmol) and the mixture was stirred at room temperature for half hour. The excess methylene chloride and TFA was evaporated by solvent exchange with chloroform for 4 times. The product was dissolved in dry methylene chloride (50 mL) and cooled down to 0° C. BnBr (2.8 g, 16.4 mmol) and $CsCO_3$ (10.7 g, 32.91 mmol) were added and the solution was stirred for 12 hrs with slow warming to room temperature. The mixture was then cooled down to 0° C. and ice-cold water (150 mL) was added. The mixture was then extracted with methylene chloride (3×50 mL) and the combined organic layers were washed with brine, dried over $NaSO_4$, filtered and the solvent was removed. Flash chromatography using a gradient of 10–20% EtOAc/Hexane gave the Compound 1B (2.7 g, 81%) as an oily liquid. $^1$H NMR (CDCl3, 300 MHz)δ: 1.26 (t, J=7.2, 3H), 2.79 (ABX, J=5.7, J=12, 2H), 3.47 (m, J=6.3, 1H), 3.56 (AB, J=13.8, 2H), 4.18 (m, J=7.2, 2H), 5.90 (d, J=15, 1H), 6.86 (dd, J=15.6, 7.5, 1H), 7.27 (m, 10H). $^{13}$C NMR, (CDCl$_3$, 75 MHz) δ: 21.4, 42, 51.7, 60.1, 60.7, 122.5, 127.3, 128.3, 128.7, 128.9, 129.7, 140.3, 150.5, 166.7. LC/MS expected mass 309.1, observed $M^{+1}$ mass: 310.1.

EDCI (0.31 g, 1.63mmol), followed by HOAT (0.22 g, 1.63 mmol) and 3-acetyl acrylic acid (0.185 g, 1.63 mmol) were added to a stirred solution of the N-benzyl protected unsaturated ester Compound 1B (0.167 g, 0.54 mmol) in dry DMF (15 mL) at 0° C. The mixture was stirred overnight (14 hrs) with slow warming from 0° C. to room temperature and quenched with ice-cold water (100 mL). The mixture was then extracted with diethyl ether (3×50 mL) and the combined ether layer was further washed with water (3×20 mL) and saturated brine solution (1×20 mL). The organic layer was dried over $NaSO_4$ and concentrated under vacuum to give a yellow liquid. Chromatography using 20–40% EtOAc/Hexane isolated pure Compound 1C (0.182 g, 82%). $^1$H NMR δ: 1.12 (t, J=7.24, 3H), 2.21 (s, 3H), 2,85–3.25 (m, 2H), 4.05 (q, J=7.24), 4.10–4.50 (AB, J=18.6), 4.85 (m, 1H), 5.65 (d, J=14.26, 1H), 6.53–7.35 (m, 12 H). $^{13}$C NMR δ: (CDCl3): 21.4, 29.3, 38.1, 50.9, 59.8, 60.7, 61.1, 123.6, 123.8, 127, 127.2, 127.6, 127.9, 128.3, 128.8, 129.0, 129.4, 132.2, 136.7, 138.5, 144.9, 165.6, 166.9, 197.7.

The uncyclized Compound 1C (0.182 g, 0.44 mmol) was dissolved in dry toluene (10 mL) and refluxed for 16 hrs. The excess toluene was removed under vacuo. A single isomer of the desired cyclized product Cpd 1 (0.164 g, 91%) was isolated by flash chromatography using 30–50% EtOAc/Hexane. $^1$H NMR (CDCl3, 300 MHz δ: 1.2 (t, J=7.14, 3H), 1.75 (s, 3H), 2.48 (ddd, J=3.41, 6.58, 1H), 2.65 (m, J=8.4, 3.41, 1H), 2.85 (m, 1H), 3.05 (dd, J=9.15, 4.27, 1H), 3.52 (m, J=8.25, 4.83, 2H), 3.95 (q, J=7.16, 2H), 4.01 (d, J=14.82, 1H), 4.85 (d, J=4.27, 1H), 5.15 (d, J=14.82, 1H), 7.01–7.42 (m, 5H). $^{13}$C NMR (CDCl3, 75 MHz), d: 14.3, 20.1, 37.5, 37.8, 38.7, 44.9, 58.2, 61.8, 94.4, 127.5, 128.2, 128.6, 129.2, 129.3, 129.6. The expected mass is 405.2, observed mass in LC/MS: 406.2.

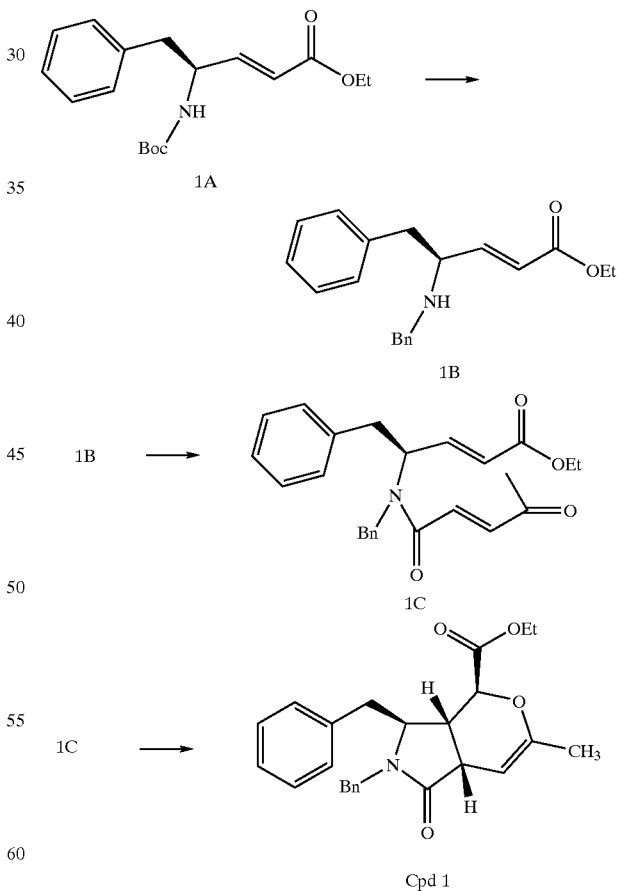

Using the procedure of Example 1 and the appropriate reagents and starting materials known to those skilled in the art, other compounds of the present invention may be prepared including, but not limited to:

| Cpd | Name | ES-MS m/z (MH+) |
|---|---|---|
| 1a | (3S,3aS,4S,7aS)-1,2,3,3a,4,7a-hexahydro-6-methyl-1-oxo-2,3-bis(phenylmethyl)-pyrano[3,4-c]pyrrole-4-carboxylic acid ethyl ester | 405.19 |
| 6 | (3S,3aR,4S,7aS)-1,2,3,3a,4,7a-hexahydro-6-methyl-3-(1-methylethyl)-1-oxo-2-(phenylmethyl)-pyrano[3,4-c]pyrrole-4-carboxylic acid ethyl ester | 357.19 |
| 7 | (3S,3aR,4S,7aS)-1,2,3,3a,4,7a-hexahydro-3-(1-methylethyl)-1-oxo-6-phenyl-2-(phenylmethyl)-pyrano[3,4-c]pyrrole-4-carboxylic acid ethyl ester | 483.10 |

EXAMPLE 2

(3S,3aR,4S,7aR)-1,2,3,3a,4,7a-Hexahydro-1-oxo-6-phenyl-2,3-bis(phenylmethyl)-pyrano[3,4-c]pyrrole-4-carboxylic acid ethyl ester (Cpd 2)

EDCI (0.53 g, 2.79 mmol), followed by HOAT (0.37 g, 2.79 mmol) and 3-benzyl acrylic acid (0.49 g, 2.79 mmol) were added to a cooled down solution (0° C.) of N-benzyl ester Compound 1B (0.247 g, 0.79 mmol) dissolved in dry DMF (20 mL). The mixture was stirred at room temperature for 19 hrs, cooled down to 0° C. and 100 mL water was added. The crude mixture was extracted with diethyl ether (3×25 mL) and the combined organic layer was washed with water, followed by brine, then dried over $Na_2SO_4$ and solvent removed under vacuo. The crude Compound 2A was then used directly in further reactions.

The crude uncyclized Compound 2A (0.085 g, 0.18 mmol) was dissolved in toluene and refluxed for 16 hrs, after chromatography using 30% EtOAc/Hexane (Rf=0.41 in 40% EtOAc/Hexane) a single isomer of Cpd 2 (0.072 g, 85%) was isolated. $^1$H NMR (CDCl3, 300 MHz) δ: 1.21 (t, J=7.12, 3 H), 2.65–2.85 (m, 4H), 2.95–3.15 (m, 3H), 3.55–3.75 (m, 3H), 3.90–4.07 (q, J=7.15, 2H), 5.11 (d, J=14.94), 5.65 (d, J=4.32, 1H), 6.85–7.75 (m, 10H). The expected LC/MS mass of the compound is 467.2, the observed mass was 467.2; the sodium salt 490.2 was also observed.

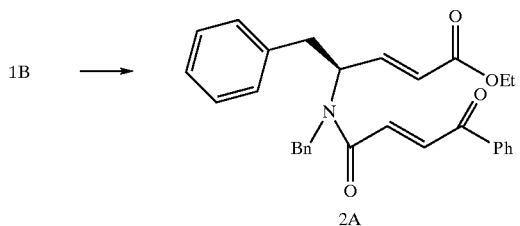

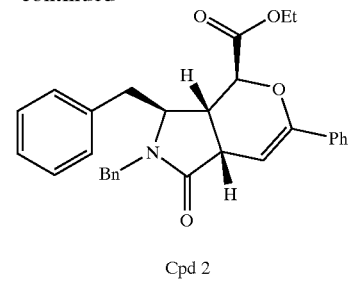

Cpd 2

Using the procedure of Example 2 and the appropriate reagents and starting materials known to those skilled in the art, other compounds of the present invention may be prepared including, but not limited to:

| Cpd | Name | ES-MS m/z (MH+) |
|---|---|---|
| 2a | (3S,3aR,4S,7aS)-1,2,3,3a,4,7a-hexahydro-1-oxo-6-phenyl-2,3-bis(phenylmethyl)-pyrano[3,4-c]pyrrole-4-carboxylic acid ethyl ester | 467.21 |
| 7 | (3S,3aR,4S,7aS)-2-[(4-bromophenyl)methyl]-1,2,3,3a,4,7a-hexahydro-1-oxo-6-phenyl-3-(phenylmethyl)-pyrano[3,4-c]pyrrole-4-carboxylic acid ethyl ester | 419.21 |
| 9 | (3S,3aR,4S,7aS)-2-[(4-bromophenyl)methyl]-1,2,3,3a,4,7a-hexahydro-6-methyl-1-oxo-3-(phenylmethyl)-pyrano[3,4-c]pyrrole-4-carboxylic acid ethyl ester | 545.12 |

EXAMPLE 3

(3S,3aR,4S,7aR)-2,3,3a,4,5,7a-hexahydro-5-hydroxy-1-oxo-6-phenyl-2,3-bis(phenylmethyl)-1H-pyrrolo[3,4-c]pyridine-4-carboxylic acid ethyl ester (Cpd 4)

Hydroxyl amine hydrochloride (0.07 g, 3eq, 1.01 mmol) and sodium bicarbonate (0.138 g, 1.65 mmol) were sequentially added to a mixture of crude uncyclized Compound 2A (0.137 g, 0.33 mmol) in 50% aqueous EtOH (10 mL) cooled down to 0° C. The mixture was stirred for 6 hrs at room temperature, 10 mL water was added at 0° C. followed by extraction with chloroform (3×20). The organic layers were combined and dried over $Na_2SO_4$. Chromatography with 5% $MeOH/CH_2Cl_2$ isolated a mixture (20:1) of isomers (0.115 g, 83%). Compound 3A was characterized: 1H NMR d: 1.25 (t, J=7.25, 3H), 1.85 (s, 3H), 2.85–3.35 (m, 2H), 4.15 (q, J=7.25, 2H), 4.40 (ABX, J=18.65, 2H), 4.72 (m, 1H), 5.15 (m, 1H), 5.82 (d, J=17.95, 1H), 5.92 (J=17.98, 1H), 6.20 (d, J=18.25, 1H,), 6.38 (d, J=18.35, 1H), 6.9–7.35(m, 10H), 8.30, (bs, N-OH). Expected mass: 420.2, observed M+1= 421.2, observed Na salt 443.2.

Hydroxyl amine hydrochloride (0.06 g, 0.88mmol) and by sodium bicarbonate (0.124 g, 1.47 mmol) were sequentially added to a mixture of the uncyclized Compound 2A (0.138 g, 0.29 mmol) dissolved in 50% aqous ethanol (10 mL) at 0° C. The ice bath was removed and the reaction mixture was stirred at room temperature for 4 hours. 5 gm of silica gel were added to the mixture and the excess of water and ethanol was removed under vacuo at 30–40° C. Methylene chloride (15 mL) was added and the mixture was further stirred at room temperature for 18 hours. The silica gel was removed by filtration and a crude product was recovered by washing with chloroform. After removal of solvent and chromatography (60–80%) EtOAc/Hexane Cpd 4 (0.11 g, 78%) was isolated. ¹H NMR, (CDCl3, 300 MHz), δ: 1.05–1.25 (t, J=7.14, 3H), 1.45 (bs, N-OH), 2.6 (dd, J=14.73, J=4.91, 1H), 2.85–2.98 (m, 2H), 3.20–3.30 (dd, J=14.73, 4.91), 3.35–3.65 (m, 1H), 3.61 (s, 1H), 3.95–4.15(m, 3H), 4.9 (d, J=14.23, 1H), 5.4 (s, 1H), 6.91–7.56 (m, 15H). The expected mass in LC/MS=482.2, observed mass=483.2.

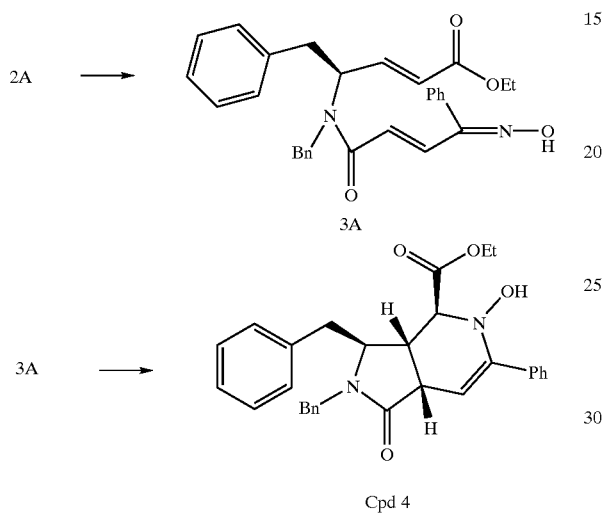

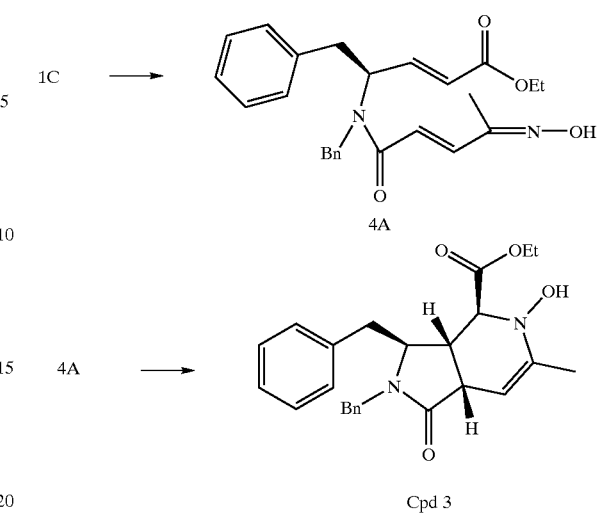

Cpd 3

EXAMPLE 4

(3S,3aR,4S,7aR)-2,3,3a,4,5,7a-hexahydro-5-hydroxy-6-methyl-1-oxo-2,3-bis(phenylmethyl)-1H-pyrrolo[3,4-c]pyridine-4-carboxylic acid ethyl ester (Cpd 3)

Hydroxyl amine hydrochloride salt (0.057 g, 0.82 mmol) and NaHCO3 (0.113 g, 1.35 mmol) were sequentially added to a cooled down mixture (0° C.) of Compound 1C (0.112gm, 0.27 mmol) dissolved in 50% EtOH/H₂O (8 mL). The ice-bath was removed, then the mixture was warmed up to room temperature and stirred for 4 hours at room temperature. 3 g silica gel was added to the mixture and the excess EtOH and water were removed in vacuo at 35–40° C. 10 mL of EtOAc was added over the impregnated silica gel and the mixture was then stirred for 24 hrs at room temperature. The silica gel was removed via filtration, followed by extraction and washing with chloroform to isolate Cpd 3. ¹H NMR (CDCl3, 300 MHz) δ: 1.15–1.35 (t, J=7.42, 3H), 1.66 (bs, N-OH), 1.95 (s, 3H), 2.05–2.26 (m, 2H), 2.65–2.80 (dd J=17.45, 10.42, 1H), 2.80–2.95 (dd, J=18.65, 10.42, 1H), 2.95–3.15 (m, J=18.65, 3.65, 1H), 4.10 (m, 2H), 4.25 (d, J=14.95, 1H), 5.15–5.25 (dd, J=14.95, 1H), 6.95–7.55 (m, 10H). The expected mass in LC/MS is 420.2, the observed mass =421.2, and Na salt 443.2.

EXAMPLE 5

(α³R,2S,3R,4R)-α-hydroxy-5-oxo-4-(2-oxopropyl)-1,2-bis(phenylmethyl)-3-pyrrolidineacetic acid (Cpd 10)

Solid Phase Synthesis

A triethyl phosphono acetate resin (350 mg, 0.80 mmol/g, 0.28 mmol) (prepared as described in Sun, et al, *J. Org. Chem.*, 1999, 64, 16, 5941–5945) suspended in 3 mL THF was treated with Kotbu (0.3 mL, 1 M) and gently stirred for 1 hr. A solution of a N-Fmoc-protected aldehyde (312 mg, 0.84 mmol) (prepared as described in Ho, Pak T. and Ngu, Kheh Yong, *J. Org. Chem.*, 1993, 58, 8, 2313–6) in 1 mL THF was added drop by drop to the reaction vessel. The mixture was shaken overnight for 14 hours, then washed sequentially with THF(20 mL), water(40 mL), THF (30 mL) and ether (30 mL). The mixture was treated with 4 mL piperidine (20% in DMF), shaken for 15 minutes and washed sequentially with DMF and THF, then dried. A ninhydrin test conducted and demonstrated the presence of the free amine Compound 5A.

Benzaldehyde (130 μl, 1.19 mmol, 10 eq) and ACOH (300 μL) were added to the amine bound resin Compound 5A (150 mg, 0.119 mmol) suspended in Trimethyl ortho formate (4 mL). The reaction mixture was shaken for 1 hr, then filtered and washed sequentially with THF (30 mL), water (30 mL) and ether (50 mL). NaCNBH3 (10 mg, 0.15 mmol), TMOF (4 mL) and 2 drops of AcOH were added to the dry resin. The mixture was shaken overnight and washed sequentially with water, 10% NaHCO3, water and ether, then dried to yield Compound 5B.

3-Acetyl acrylic acid (202 mg, 1.717 mmol), DIEA (400 μL), HATU (625 mg, 1.71 mmol) and DMF 8 mL were sequentially. added to the resin bound N-benzyl protected ester of phenyl alanine Compound 5B (496 mg, 0.354 mL).

The mixture was shaken for 2 hrs to give Compound 5C.

The resin bound intermediate Compound 5C (250 mg, 0.148 mmol) was heated in DMF at 60° C. for 15 hr. The final product was cleaved using 50% TFA and purified by HPLC (40%–70% MeCN) in $H_2O$ over 30 minutes (eluting at $R_t$=13 min). After evaporation and drying, Cpd 10 (21 mg, 36%) was isolated as a yellow glass-like pure product. $^1$H NMR ($CD_3OD$, 300 MHz) δ: 2.10 (s, 3H), 2.50 (m, 1H), 2.65 (ABX, 1H), 2.85–2.95 (m, 1H), 3.20 (dd, ABX, 1H), 3.55 (d, 1H), 3.85 (m, 1H), 4.30 (m, 1H), 4.95–5.15 (m, 1H), 7.03–7.40 (m, 10 H). The calculated molecular weight was 395.2, the final molecular weight was 395.3 (M+1). $C^{13}$ NMR ($CD_3OD$, 75 MHz) δ: 30.2, 38.9, 40.3, 44.0, 45.9, 46.1, 61.2, 70.8, 128.0, 128.6, 129.0, 129.8, 129.9, 130.9, 137.6, 138.3, 176.2, 177.9, 209.0. The expected LC/MS mass was 395, the observed M+1 mass was 396.

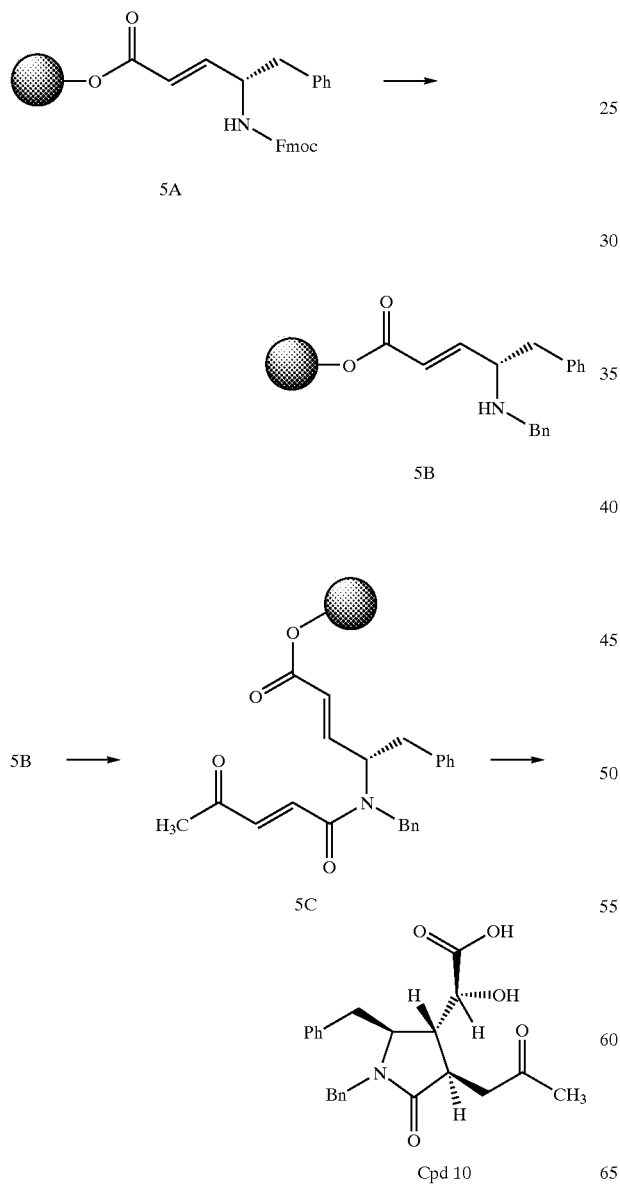

EXAMPLE 6

($α^3$R, 2S,3S,4R)-α-(methylamino)-5-oxo-4-(2-oxopropyl)-1,2-bis(phenylmethyl)-3-pyrrolidineacetic acid (Cpd 11)

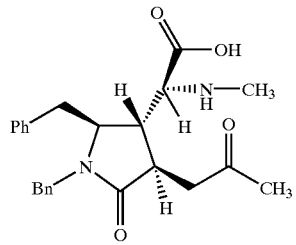

AcOH (0.5 mL) and methyl amine (250 μL, 2.9 mmol) were added to a mixture of N-benzyl protected resin bound triene Compound 5C (0.5 g, 0.29mmol) in DMF (8 mL). The mixture was shaken for 4 days, then filtered and washed. A crude product was cleaved from the resin with 50% TFA and purified via HPLC (30–45% $CH_3CN/H_2O$) for 5 hours (eluting at $R_t$=21.8 min) to isolate the major product Cpd 11 (31 mg, 26%). $^1$H NMR ($CDCl_3$, 300 MHz) δ: 1.90–2.25 (dd, 1H), 2.26 (s, 3H), 2.40–2.51 (dd, 1H), 2.52 (s, 3H), 3.30 (m, 5H), 3.60 (m, 1H), 3.85, (m, 2H), 5.40(d, 1H), 6.90–7.50 (m, 10 H). LC/MS expected mass: 409, observed mass (M+1) 410.

EXAMPLE 7

(3S,3aR,4S,7aR)-2,3,3a,4,5,7a-hexahydro-5-hydroxy-6-methyl-1-oxo-2,3-bis(phenylmethyl)-1H-pyrrolo[3,4-c]pyridine-4-carboxylic acid (Cpd 5)

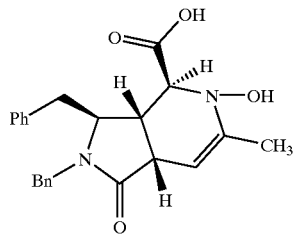

Acetic acid (200 μL) and $NH_2OH.H_2O$ (100 μL, 50 wt%, 1.63 mmol) were added to a mixture of N-benzyl protected resin bound triene Compound 5C (0.25 g, 0.198 mmol) in DMF (4 mL) was added over 4 days. The resin was then filtered and washed sequentially with THF and water.

A crude product was cleaved from the resin with 50% TFA and purified via HPLC (30–45% $CH_3CN/H_2O$) for 0.5 hours (eluting at $R_t$=17 min, having MW 392) to isolate the major product Cpd 5 (11 mg, 19%). $^1$H NMR ($CDCl_3$, 300 MHz) δ: 2.15 (s, 3H), 2.16–2.45 (m, 1H), 2.45–3.00 (m, 2H), 3.00–3.30 (m, 2H), 4.05, (m, 1H), 4.10 (d, 1H), 4.60 (d, 1H), 5.10 (d, 1H), 6.60–7.40 (m, 10H). The expected LC/MS mass was 392, the observed M+1 mass was 393.

EXAMPLE 8

(α³R,2S,3R,4R)-α-hydroxy-5-oxo-4-(2-oxo-2-phenylethyl)-1,2-bis(phenylmethyl)-3-pyrrolidineacetic acid (Cpd 12)

3-Benzyl acrylic acid (500 mg, 3.6 mmol), DIEA (800 µL), HATU (1.302 g, 1.71 mmol) and DMF 20 mL were added to the resin bound N-benzyl protected ester of phenylalanine Compound 5B (500 mg, 0.36 mmol). The mixture was shaken for 4 hours to produce the intermediate Compound R8A.

The intermediate Compound 8A (210 mg, 0.12 mmol) in DMF (4 mL) was allowed to stand at room temperature for 1 week. The resin was then washed sequentially with THF and water. A crude product was cleaved from the resin with 50% TFA and purified via HPLC (30–70% $CH_3CN/H_2O$) for 0.5 hours (eluting at $R_f$=22 min, having MW 457) to isolate the major product Cpd 12(8 mg, 14.6%). $^1H$ NMR ($CDCl_3$, 300 MHz) δ: 1.75–1.95 (dd, 1H), 2.28 (m, 1H), 2.75–2.95 (ABX, 1H), 2.95–3.15 (m, 2H), 3.15–3.30 (d, ABX, 1H), 3.85 (m, 1H), 3.90–4.00 (m, 1H), 4.20 (m, 1H), 5.15–5.35 (m, 1H), 6.90–7.70 (m, 10 H). The expected mass in LC/MS is 457, the observed M+1 mass=458

5B →
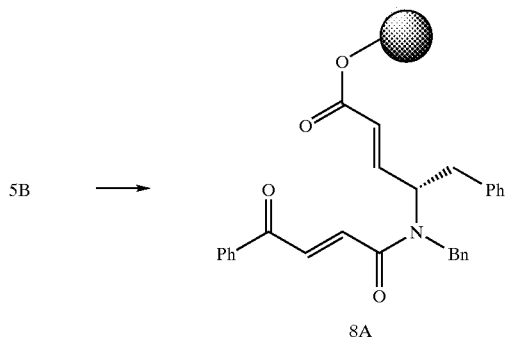
8A

8A →
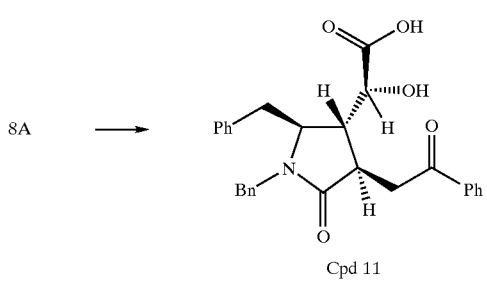
Cpd 11

EXAMPLE 9

(α³R,2S,3S,4R)-α-(methylamino)-5-oxo-4-(2-oxo-2-phenylethyl)-1,2-bis(phenylmethyl)-3-pyrrolidineacetic acid (Cpd 13)

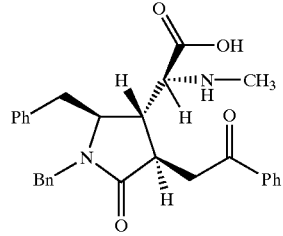

Methyl amine (10 eq, 0.57 mmol) was added to a resin bound intermediate Compound 8A (100 mg, 0.057 mmol) in DMF (2 mL). The mixture was shaken for 4 days at room temperature, then washed sequentially with THF (20 mL) and water. A crude product was cleaved from the resin with 50% TFA and purified via HPLC (30–70% $CH_3CN/H_2O$) for 0.5 hours to isolate the major product Cpd 13 (6 mg, 23%). 1.95–2.05 (m, 1H), 2.50 (s, 3H), 3.25 (d, 1H), 3.40–3.56 (d, 1H), 3.60 (m, 2H), 3.80 (m, 2H), 3.90 (m, 1H), 5.40 (d, 1H), 7.00–8.05 (m, 10 H). The expected LC/MS mass was 470, the observed M+1 mass was 471.

What is claimed is:

1. A method for generating densely functionalized pyrrolidine intermediates selected from the group consisting of Formula (I) and Formula (II):

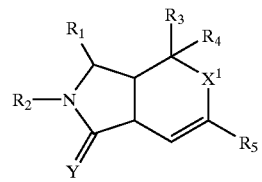

Formula (I)

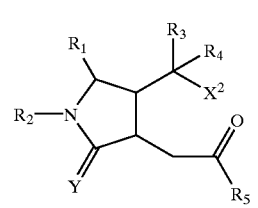

Formula (II)

wherein $R_1$ is selected from the group consisting of a standard, natural (L) and non-natural (D), non-hydrogen amino acid side chain (wherein the amino acid side chain is optionally substituted with a suitable protecting group), hydrogen and —$(C_{1-8})$alkyl {wherein $C_{1-8}$alkyl is optionally substituted with 1 to 2 substituents selected from the group consisting of —$CO_2H$ (wherein $CO_2H$ is optionally substituted with a suitable protecting group), -phenyl-$R_6$, -heteroaryl-$R_6$ and hydroxy (wherein hydroxy is optionally substituted with a suitable protecting group)}; alternatively, $R_1$ and $R_2$ may be joined to form a heterocyclyl ring;

$R_6$ is one to two substituents selected from the group consisting of hydrogen, —$(C_{1-8})$alkyl, —O—$(C_{1-8})$alkyl, halogen, hydroxy and nitro;

$R_2$ is selected from the group consisting of hydrogen (wherein hydrogen is optionally replaced with a suitable protecting group), —$(C_{1-8})$alkyl, —$(C_{1-8})$alkyl-Ph—$R_6$, —C(O)—$(C_{1-8})$alkyl, —C(O)—Ph—$R_6$, —C(O)O—$(C_{1-8})$alkyl, —C(O)O—Ph—$R_6$, —C(O)O—$(C_{1-8})$alkyl-Ph—$R_6$ and —SO$_2$—Ph—$R_6$;

$R_3$ is selected from the group consisting of —C(O)—N$(R_7R_8)$, —CO$_2$H (wherein CO$_2$H is optionally substituted with a suitable protecting group), —C(O)—O—$(C_{1-8})$alkyl and cyano;

$R_7$ is selected from hydrogen, —$(C_{1-8})$alkyl, —$(C_{1-8})$alkyl-Ph—$R_6$, hydroxy (wherein hydroxy is optionally substituted with a suitable protecting group) or a suitable protecting group;

$R_8$ is selected from hydrogen, —$(C_{1-8})$alkyl, —$(C_{1-8})$alkyl-Ph—$R_6$ or a suitable protecting group;

$R_4$ is selected from the group consisting of hydrogen, —$(C_{1-8})$alkyl and —$(C_{1-8})$alkyl-Ph—$R_6$;

$R_5$ is selected from the group consisting of —$(C_{1-8})$alkyl and —Ph—$R_6$;

Y is optionally present and is selected from the group consisting of O and S;

$X^1$ is selected from the group consisting of —O—, —N(H)—(wherein NH is optionally substituted with a suitable protecting group), —N(—OH)— (wherein hydroxy is optionally substituted with a suitable protecting group), —N(—O—$(C_{1-8})$alkyl)—, —N(—$C_{1-8}$alkyl-aryl-$R_6$)— and —N(—O—$(C_{1-8})$alkyl-aryl-$R_6$)—; and, $X^2$ is selected from the group consisting of —OH (wherein OH is optionally substituted with a suitable protecting group), —NH$_2$ (wherein NH$_2$ is optionally substituted with a suitable protecting group), —NH(—OH) (wherein NH and OH are optionally substituted with a suitable protecting group), —NH(—$C_{1-8}$alkyl) (wherein NH is optionally substituted with a suitable protecting group) and —NH(—$C_{1-8}$alkyl-aryl-$R_6$) (wherein NH is optionally substituted with a suitable protecting group);

and pharmaceutically acceptable salts and diastereomers thereof;

wherein the method for generating an intermediate selected from the group consisting of Formula (I) and Formula (II) is either a resin-bound or an in-situ method comprising:

(a) preparing a compound of Formula (III):

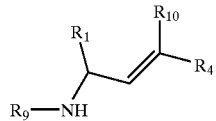

Formula (III)

wherein $R_1$ and $R_4$ are as previously described; wherein $R_9$ is selected from $R_2$ (for an in-situ method) or (for a resin-bound method) is selected from —SO$_2$—Ph—CO$_2$—(resin) or —SO$_2$—Ph—C(O)—NH—(resin); and, wherein $R_{10}$ is selected from $R_3$ (for an in-situ method) or (for a resin-bound method) is selected from —CO$_2$—(resin), —C(O)—NH—(resin) or —C(N)—(resin); and, (b) acylating the compound of Formula (III) to prepare a compound of Formula (IV):

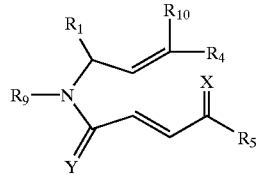

Formula (IV)

wherein Y, $R_1$, $R_4$, $R_5$, $R_9$ and $R_{10}$ are as previously described; and, wherein X is selected from the group consisting of O, N(H) (wherein NH is optionally substituted with a suitable protecting group), N(—OH) (wherein hydroxy is optionally substituted with a suitable protecting group), N(—O—$(C_{1-8})$alkyl), N(—$C_{1-8}$alkyl-aryl-$R_6$) and N(—O—$(C_{1-8})$alkyl-aryl-$R_6$);

(c) reacting the compound of Formula (IV) (with the proviso that the method is a resin-bound method) with the appropriate starting materials, using the appropriate reagents and conditions and cleaving the compound of Formula (IV) (with the proviso that the method is a resin-bound method) from the resin to prepare the intermediate selected from the group consisting of Formula (I) and Formula (II); or, (d) refluxing the compound of Formula (IV) (with the proviso that the method is an in-situ method) using the appropriate reagents and conditions to prepare the intermediate selected from the group consisting of Formula (I) and Formula (II); wherein the intermediate is selected from a kinetic product (a trans isomer prepared at a reflux temperature of ≦80° C.) or a thermodynamic product (a cis isomer prepared at a reflux temperature of >80° C.);

alternatively, the method for preparing an intermediate of Formula (I) further comprises preparing a compound selected from Formula (IV) wherein X is NH(—OH); and, adding silica gel in the appropriate amount at the appropriate time and temperature to prepare the intermediate of Formula (I) by cycloaddition; and, alternatively, the method for preparing an intermediate of Formula (II) further comprises hydrolyzing an intermediate of Formula (I) under the appropriate conditions to prepare the intermediate of Formula (II).

2. The method of claim 1 wherein $R_1$ is selected from the group consisting of a standard, natural (L) and non-natural (D), non-hydrogen amino acid side chain (wherein the amino acid side chain is optionally substituted with a suitable protecting group), hydrogen and —$(C_{1-4})$alkyl {wherein $C_{1-4}$alkyl is optionally substituted with 1 to 2 substituents selected from the group consisting of —CO$_2$H (wherein CO$_2$H is optionally substituted with a suitable protecting group), -phenyl-$R_6$, -heteroaryl-$R_6$ and hydroxy (wherein hydroxy is optionally substituted with a suitable protecting group)}; alternatively, $R_1$ and $R_2$ may be joined to form a heterocyclyl ring.

3. The method of claim 1 wherein $R_1$ is selected from a standard, natural (L) and non-natural (D), non-hydrogen amino acid side chain optionally substituted with a suitable protecting group.

4. The method of claim 3 wherein the amino acid side chain is selected from Ala, Val, Phe, Tyr, Ser, Thr, Asp, Glu and His.

5. The method of claim 1 wherein $R_6$ is one to two substituents selected from the group consisting of hydrogen, —$(C_{1-4})$alkyl, —O—$(C_{1-4})$alkyl, halogen, hydroxy and nitro.

6. The method of claim 1 wherein $R_6$ is one to two substituents selected from the group consisting of hydrogen, —O—$(C_{1-4})$alkyl, halogen and nitro.

7. The method of claim 1 wherein $R_6$ is one to two substituents selected from the group consisting of hydrogen, methoxy, bromine and nitro.

8. The method of claim 1 wherein $R_2$ is selected from the group consisting of hydrogen (wherein hydrogen is optionally replaced with a suitable protecting group), —$(C_{1-4})$alkyl, —$(C_{1-4})$alkyl-Ph—$R_6$, —C(O)—$(C_{1-4})$alkyl, —C(O)—Ph—$R_6$, —C(O)O—$(C_{1-4})$alkyl, —C(O)O—Ph—$R_6$, —C(O)O—$(C_{1-4})$alkyl-Ph—$R_6$ and —$SO_2$—Ph—$R_6$.

9. The method of claim 1 wherein $R_2$ is selected from the group consisting of —$(C_{1-4})$alkyl, —$(C_{1-4})$alkyl-Ph—$R_6$, —C(O)O—$(C_{1-4})$alkyl, —C(O)O—$(C_{1-4})$alkyl-Ph—$R_6$ and —$SO_2$—Ph—$R_6$.

10. The method of claim 1 wherein $R_2$ is selected from —$(C_{1-4})$alkyl-Ph—$R_6$.

11. The method of claim 1 wherein $R_3$ is selected from the group consisting of —C(O)—N($R_7R_8$), —$CO_2$H (wherein $CO_2$H is optionally substituted with a suitable protecting group), —C(O)—O—$(C_{1-4})$alkyl and cyano.

12. The method of claim 1 wherein $R_3$ is selected from the group consisting of —$CO_2$H (wherein $CO_2$H is optionally substituted with a suitable protecting group), —C(O)—O—$(C_{1-4})$alkyl and cyano.

13. The method of claim 1 wherein $R_3$ is selected from —C(O)—O—$(C_{1-4})$alkyl.

14. The method of claim 1 wherein $R_7$ is selected from hydrogen, —$(C_{1-4})$alkyl, —$(C_{1-4})$alkyl-Ph—$R_6$, hydroxy (wherein hydroxy is optionally substituted with a suitable protecting group) or a suitable protecting group.

15. The method of claim 1 wherein $R_7$ is selected from hydrogen, —$(C_{1-4})$alkyl or a suitable protecting group.

16. The method of claim 1 wherein $R_7$ is hydrogen.

17. The method of claim 1 wherein $R_8$ is selected from hydrogen, —$(C_{1-4})$alkyl, —$(C_{1-4})$alkyl-Ph—$R_6$ or a suitable protecting group.

18. The method of claim 1 wherein $R_8$ is selected from hydrogen, —$(C_{1-4})$alkyl or a suitable protecting group.

19. The method of claim 1 wherein $R_8$ is hydrogen.

20. The method of claim 1 wherein $R_4$ is selected from the group consisting of hydrogen, —$(C_{1-4})$alkyl and —$(C_{1-4})$alkyl-Ph—$R_6$.

21. The method of claim 1 wherein $R_4$ is selected from the group consisting of hydrogen and —$(C_{1-4})$alkyl.

22. The method of claim 1 wherein $R_4$ is hydrogen.

23. The method of claim 1 wherein $R_5$ is selected from the group consisting of —$(C_{1-4})$alkyl and —Ph—$R_6$.

24. The method of claim 1 wherein Y is present and is selected from the group consisting of O and S.

25. The method of claim 24 wherein Y is O.

26. The method of claim 1 wherein $X^1$ is selected from the group consisting of —O—, —N(H)—, (wherein NH is optionally substituted with a suitable protecting group), —N(—OH)— (wherein hydroxy is optionally substituted with a suitable protecting group), —N(—O—$(C_{1-4})$alkyl)—, —N(—$C_{1-4}$alkyl-aryl-$R_6$)— and —N(—O—$(C_{1-4})$alkyl-aryl-$R_6$)—.

27. The method of claim 1 wherein $X^1$ is selected from the group consisting of —O— and —N(—OH)— (wherein hydroxy is optionally substituted with a suitable protecting group).

28. The method of claim 1 wherein $X^1$ is selected from the group consisting of —O— and —N(—OH)—.

29. The method of claim 1 wherein $X^2$ is selected from the group consisting of OH (wherein OH is optionally substituted with a suitable protecting group), —$NH_2$ (wherein $NH_2$ is optionally substituted with a suitable protecting group), —NH(—OH) (wherein NH and OH are optionally substituted with a suitable protecting group), —NH(—$C_{1-4}$alkyl) (wherein NH is optionally substituted with a suitable protecting group) and —NH(—$C_{1-4}$alkyl-aryl-$R_6$) (wherein NH is optionally substituted with a suitable protecting group).

30. The method of claim 1 wherein $X^2$ is selected from the group consisting of OH (wherein OH is optionally substituted with a suitable protecting group), —NH(—OH) (wherein NH and OH are optionally substituted with a suitable protecting group) and —NH(—$C_{1-4}$alkyl-aryl-$R_6$) (wherein NH is optionally substituted with a suitable protecting group).

31. The method of claim 1 wherein the intermediates selected from Formula (I) are selected from Formula (Ia):

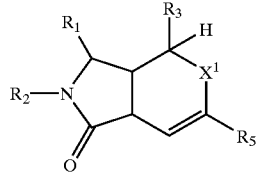

Formula (Ia)

wherein $X^1$, $R_1$, $R_2$, $R_3$ and $R_5$ are dependently selected from the group consisting of:

| $X^1$ | $R_1$ | $R_2$ | $R_3$ | $R_5$ |
|---|---|---|---|---|
| —O— | —$CH_2$Ph | —$CH_2$Ph | —C(O)OEt | $CH_3$; |
| —O— | —$CH_2$Ph | —$CH_2$Ph | —C(O)OEt | Ph; |
| —N(OH)— | —$CH_2$Ph | —$CH_2$Ph | —C(O)OEt | $CH_3$; |
| —N(OH)— | —$CH_2$Ph | —$CH_2$Ph | —C(O)OEt | Ph; |
| —N(OH)— | —$CH_2$Ph | —$CH_2$Ph | —C(O)OH | $CH_3$; |
| —O— | —CH($CH_3$)$_2$ | —$CH_2$Ph | —C(O)OEt | $CH_3$; |
| —O— | —CH($CH_3$)$_2$ | —$CH_2$Ph | —C(O)OEt | Ph; |
| —O— | —$CH_2$Ph | —$CH_2$(4-Br)Ph | —C(O)OEt | Ph; |
| and, | | | | |
| —O— | —$CH_2$Ph | —$CH_2$(4-Br)Ph | —C(O)OEt | $CH_3$; | and pharmaceutically acceptable salts and diastereomers thereof.

32. The method of claim 1 wherein the intermediates selected from Formula (II) are selected from Formula (IIa):

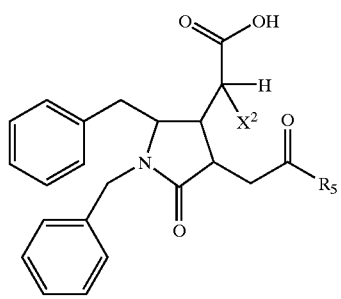

Formula (IIa)

wherein $X^2$ and $R_5$ are dependently selected from the group consisting of:

| $X^2$ | $R_5$ |
|---|---|
| —OH | $CH_3$; |
| —NH—$CH_3$ | $CH_3$; |
| —OH | Ph; |
| and, | |
| —NH—$CH_3$ | Ph; | and pharmaceutically acceptable salts and diastereomers thereof.

33. The method of claim 1 wherein the compounds selected from Formula (IV) are selected from Formula (IVa):

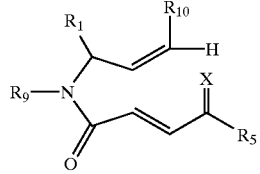

Formula (IVa)

wherein X, $R_1$, $R_5$, $R_9$ and $R_{10}$ are dependently selected from the group consisting of:

| X | $R_1$ | $R_5$ | $R_9$ | $R_{10}$ |
|---|---|---|---|---|
| O | —$CH_2$Ph | —$CH_3$ | —$CH_2$Ph | —$CO_2$—$CH_2$—$CH_3$; |
| N(OH) | —$CH_2$Ph | —$CH_3$ | —$CH_2$Ph | —$CO_2$—$CH_2$—$CH_3$; |
| O | —$CH_2$Ph | —Ph | —$CH_2$Ph | —$CO_2$—$CH_2$—$CH_3$; |
| O | —$CH(CH_3)_2$ | —$CH_3$ | —$CH_2$Ph | —$CO_2$—$CH_2$—$CH_3$; |
| O | —$CH(CH_3)_2$ | —Ph | —$CH_2$Ph | —$CO_2$—$CH_2$—$CH_3$; |
| O | —$CH(CH_3)_2$ | —$CH_3$ | —$CH_2$(4-Br)Ph | —$CO_2$—$CH_2$—$CH_3$; |
| O | —$CH(CH_3)_2$ | —Ph | —$CH_2$(4-Br)Ph | —$CO_2$—$CH_2$—$CH_3$; |
| and, | —$CH_2$Ph | —$CH_3$ | —$CH_2$Ph | —$CO_2$—$CH_2$—$CH_3$; | and pharmaceutically acceptable salts and enantiomers thereof.

34. The method of claim 1 wherein the method further comprises a method for using the intermediates selected from the group consisting of Formula (I) and Formula (II) to synthesize compound libraries.

* * * * *